United States Patent
Rickert

(10) Patent No.: US 9,436,910 B2
(45) Date of Patent: Sep. 6, 2016

(54) METHOD, DEVICE AND DATABASE FOR RECONSTRUCTING INTENDED ACTIVITIES FROM NEURAL SIGNALS USING FREQUENCIES OF REPRESENTATIONS

(71) Applicant: Cortec GmbH, Freiburg (DE)

(72) Inventor: Jörn Rickert, Freiburg (DE)

(73) Assignee: Cortec GmbH, Freiburg (DE)

( * ) Notice: Subject to any disclaimer, the term of this patent is extended or adjusted under 35 U.S.C. 154(b) by 0 days.

(21) Appl. No.: 14/451,478

(22) Filed: Aug. 5, 2014

(65) Prior Publication Data
US 2015/0032677 A1 Jan. 29, 2015

Related U.S. Application Data

(63) Continuation of application No. PCT/EP2013/052484, filed on Feb. 7, 2013.

(30) Foreign Application Priority Data

Feb. 7, 2012 (DE) .................. 10 2012 100 999

(51) Int. Cl.
G06F 17/00 (2006.01)
G06N 3/08 (2006.01)
H04N 21/422 (2011.01)
(Continued)

(52) U.S. Cl.
CPC .............. *G06N 3/08* (2013.01); *A61B 5/165* (2013.01); *G06F 17/30312* (2013.01); *H04N 21/42201* (2013.01)

(58) Field of Classification Search
CPC . H04N 21/42201; G06F 3/013; G06N 3/061

USPC ............................ 706/12, 45, 62
See application file for complete search history.

(56) References Cited

U.S. PATENT DOCUMENTS

2003/0078522 A1   4/2003  Mitra
2009/0221928 A1*  9/2009  Einav .............. A61B 5/0484
                                                600/544
(Continued)

FOREIGN PATENT DOCUMENTS

DE      10200702886 A1    1/2009

OTHER PUBLICATIONS

Wolpaw, J. R., Birbaumer, N., McFarland, D. J., Pfurtscheller, G., & Vaughan, T. M. (2002). Brain-computer interfaces for communication and control. Clinical neurophysiology, 113(6), 767-791.*

(Continued)

*Primary Examiner* — David Vincent
(74) *Attorney, Agent, or Firm* — Myers Wolin, LLC

(57) ABSTRACT

There is provided a method for reconstructing intended activities from a first representation of neural signals which is indicative of an intended activity to a second representation, wherein for second representations, a degree of agreement between the first representation and each second representation from a plurality of predetermined second representations that are indicative of intended activities is determined on the basis of a predetermined agreement criterion, and a second representation of neural signals is selected from the plurality of second representations on the basis of the degree of agreement, which selected second representation is the reconstructed intended activity.

25 Claims, 2 Drawing Sheets

(51) Int. Cl.
  *A61B 5/16*  (2006.01)
  *G06F 17/30* (2006.01)

(56) References Cited

U.S. PATENT DOCUMENTS

2010/0094097 A1    4/2010  Liu
2011/0307079 A1*  12/2011  Oweiss ................. A61B 5/048
                                                  623/27
2013/0211238 A1*   8/2013  DeCharms ........... A61B 5/4824
                                                 600/418

OTHER PUBLICATIONS

Vallery, H., Van Asseldonk, E. H., Buss, M., & van der Kooij, H. (2009). Reference trajectory generation for rehabilitation robots: complementary limb motion estimation. Neural Systems and Rehabilitation Engineering, IEEE Transactions on, 17(1), 23-30.*

Vallery, H., & Buss, M. (Oct. 2006). Complementary limb motion estimation based on interjoint coordination using principal components analysis. InComputer Aided Control System Design, 2006 IEEE International Conference on Control Applications, 2006 IEEE International Symposium on Intelligent Control, 2006 IEEE (pp. 933-938). IEEE.*

Gilja, V., Nuyujukian, P., Chestek, C. A., Cunningham, J. P., Byron, M. Y., Fan, J. M., . . . & Shenoy, K. V. (2012). A high-performance neural prosthesis enabled by control algorithm design. Nature neuroscience, 15(12), 1752-1757.*

International Search Report with Written Opinion for International Application No. PCT/EP2013/052484, mailed May 31, 2013.

Tiziano D'Albis, "A Predictive Speller For A Brain-Computer Interface Based On Motor Imagery", Master Graduation Thesis, AI & R Lab, Laboratorio di Intelligenza Artificiale e Robotica del Politectnico di Milano, 2009, pp. 1-153.

Daniella Meeker, "Cognitive Neural Prosthetics: Brain Machine Interfaces Based on Parietal Cortex", Thesis, California Institute of Technology, Pasadena, California, 2005, pp. 1-101.

German search report, dated Oct. 12, 2012, for German Application 10 2012 100 999.6.

* cited by examiner

METHOD, DEVICE AND DATABASE FOR RECONSTRUCTING INTENDED ACTIVITIES FROM NEURAL SIGNALS USING FREQUENCIES OF REPRESENTATIONS

CROSS REFERENCE TO RELATED APPLICATIONS

The present application is a continuation of International Application No. PCT/EP2013/052484, filed on Feb. 7, 2013, which claims priority to German Patent Application No. 10 2012 100 999.6, filed on Feb. 7, 2012, the contents of each of which are incorporated herein by reference.

FIELD OF THE INVENTION

The invention relates to a method and a signal processing means for reconstructing representations of neural signals. Furthermore, the invention relates to a database for use in a method according to the invention for reconstructing representations of neural signals.

PRIOR ART AND BACKGROUND OF THE INVENTION

Notional (intended) activities such as movements, speech, emotions or visual imaginations can be derived using neurobiological methods from the brain activity of human beings and can be reconstructed by approximation. Detection systems known from prior art allow the spatio-temporal detection of the brain activities of a human being in order to thereby derive signals representative of the intended movement, speech, emotion or visual imagination. For example, foil electrodes or depth electrodes can be provided which preferably detect with a high temporal resolution, approximately within the range between 1 Hz and 1000 Hz, the brain activities and provide them as electrical signals for further processing.

Known methods and methods for the reconstruction of movements, speech, etc. from brain activities are described in "Brain-Machine Interface Engineering (Synthesis Lectures on Biomedical Engineering); Justin C. Sanchez, at al.; Morgan & Claypool Publishers, 1st Edition, November 2006", "Toward Brain-computer interfacing (Neural information Processing); Guido Dornhege et al.; The MIT Press, 1st edition, July 2007" and "Brain-computer Interfaces: An international assessment of research and development trends; Theodore W. Berger et al.; Springer Netherlands, 1st edition, November 2008".

With the devices for deriving brain activities known from prior art, the latter are measured and passed onto an evaluation unit, for example, to a computer system. For this purpose, standard appliances such as magnetic resonance tomographs (MRI) are used, which measure the local brain activity indirectly by the consumption of oxygen (functional MRI). Furthermore, electrophysiological devices can be used to measure the local brain currents (electroencephalography, electrocorticography, measurement of local field potentials or measurement of single-cell activities by intracortical electrodes), amplify them, and then send them to the evaluation unit.

The reconstruction is performed by means of a model for translation of the measured brain activities into movements, sound/words, emotions, or images [in the following in summary referred to as states or activities], which usually operates in the evaluation unit. The model is usually a mathematical algorithm which converts the measured brain activities in real time using a data processing means (computer and/or embedded system) into states/activities.

For the generation of the model, various methods are known. For example, methods known from signal analysis, such as "reverse correlation" or adaptation of, mostly linear filters, can be used to generate the model of the signal analysis.

The models, on the one hand, reflect the function of the measured brain activities, or naive, are calculated without assumptions about the function of the measured brain activities, by linking these to various preset training stimuli, or can be created by a combination of both. In the end, the model stands as a translator for the measured brain activities into the respectively selected states/activities.

A disadvantage of the reconstruction methods known from prior art is the high fuzziness or inaccuracy, respectively, of the reconstruction results. This has several reasons that cannot be overcome by the known methods.

With functional magnetic resonance tomography, the activity can be measured in all areas of the brain, however, only with a very poor temporal resolution in the range of seconds—while the brain operates is in the range of milliseconds or less. Although the spatial resolution of the brain activity is good and is constantly being improved, it nevertheless has a magnitude in the range of cubic millimeters—while the functional structures in the brain have a magnitude in the range of a few micrometers.

Electro-physiological measurement methods have similar shortcomings. With these—also for measurements with a high number of electrodes (several hundred)—only a fraction of the brain activity of selected areas can be recorded. Due to technical reasons, therefore, all measurements can only detect incomplete brain activities.

A further issue is the inaccuracy of the measurement. Brain activities have very low current flows which have to be measured under difficult conditions (in living tissue in a moving body). This means that the signals cannot be measured accurately and are usually contaminated with artifacts.

A further factor for the inaccuracy or fuzziness of the measurements is the fact that the brain activity for one and the same stimulus can be different. This phenomenon is either referred to as an intrinsic noise ("neural noise"), or as a physiologically relevant activity due to the ongoing and parallel processing of various states (see "Dynamics of ongoing activity: explanation of the large variability in evoked cortical responses; Arieli A. et al.; Science, 27 Sep. 1996, pages 1868-1871").

These features for the detection of brain activity entail always being subject to uncertainty/fuzziness. As a result, for example, a correlation coefficient is obtained within the range of 0.5 for the reconstruction of movements, or decoding accuracy for vowels only within the range of 80%.

OBJECT OF THE INVENTION

Therefore, it is an object of the invention to provide solutions which at least partially avoid the disadvantages known from prior art, and by means of which improved or results with a higher resolution are enabled for a reconstruction of the brain activities of a human being.

SOLUTION ACCORDING TO THE INVENTION

This object is achieved according to the invention by a method for the reconstruction of the intended activities of a first representation of neural signals, a database for use in a method for reconstruction of intended activities from a first representation of neural signals, and by a signal processing means for reconstruction of intended activities from a first representation of neural signals according to the independent claims. Preferred embodiments of the invention are defined in the respective dependent claims.

Thus, a method for reconstruction of intended activities from a first representation of neural signals (S) which are indicative of an intended activity is provided, wherein the first representation is generated using a predetermined procedure from the neural signals, for second representations from a plurality of predetermined second representations, each of which being representative of a predetermined activity, wherein the predetermined second representations are generated from predetermined activities, a degree of correspondence is determined respectively between the respective second representation and the first representation according to a predetermined correspondence criterion, and depending on the degree of correspondence, a second representation of the neural signals from the plurality of second representations is selected as the second representation representative of the intended activity, and the activity represented by the selected representation is reconstructed as the intended activity.

Here, the activities are the generic term for activities executable by human beings, perceptions or mental imaginations. Examples for these are movements, speech (more precisely, speaking), emotions, pictures (more precisely, vision), smells and tactile perception. The representations of high resolution describe (represent) these activities. For speech, these are, for example sonograms, for movements, e.g., trajectories (of the limbs) and for vision images.

Intended activities are intended or imaginary activities. The first representation which is derived from the neural signals (that is, from the brain activity of the human being) is capable of describing the intended activity only inaccurately. Herein, it is referred to as indicative of an intended activity. Herein, it is referred to as a fuzzy representation of an intended activity. The second representations are obtained on the basis of activities performed, but not from neural signals but rather from technical records of real or emulated activities. Herein, they are referred to as sharp representations, in the sense that every second representation is associated with an activity.

The first representations and the second representations are similar in the sense that they can be interpreted by means of the same methods in terms of activities.

By selecting a second representation which is representative of a predetermined activity, thus, the activity indicated by the first representation, thus, only with uncertainty, is replaced by a predetermined activity. This predetermined activity can be performed by a technical tool. Thereby, the tool, for example speakers or a display device which are to perform or at least to aid the patient in performing an intended activity, may be provided with sharply reconstructed activity reconstructions. Thereby, it is avoided that fuzzy reconstructions are processed by the tool, and, thus, for example, wrong or inarticulate words or sounds are output to a speaker.

Determining the degree of correspondence in accordance with the correspondence criterion may comprise determining a total correspondence probability for each second representation from the plurality of second representations, wherein the total correspondence probability from a combination of first partial probabilities, which are created for each second representation from the plurality of second representations, and wherein the total correspondence probability for each second representation indicates the probability with which the respective second representation of the first representation is assignable.

Thereby, the selection of the second reconstruction can be further improved.

Advantageously, the second representation is selected with the highest overall probability correspondence.

Each of the first partial probabilities may be weighted by a weighting factor, wherein the weighting factor may be selected to be different for each partial probability.

Thus, it is advantageously possible to determine the overall correspondence probability, for example, depending on the situation differently by the partial probabilities being weighted differently depending on the situation.

Forming the first partial probabilities may comprise at least one of
   determining a partial probability based on the frequency of the second representation within the plurality of predetermined second representations,
   determining a partial probability based on semantic relationships of the second representation to already selected sects and representations, and
   determining a partial probability based on a similarity of the second representation to the first representation.

It has proven to be advantageous when prior to the selection of the second representation from the plurality of second representations, it is verified, whether the total correspondence probability of the second representation to be selected exceeds a predetermined threshold, wherein when the predetermined threshold is not exceeded, the first representation is the intended reconstructed activity.

On the basis of the respectively determined total correspondence probability, the number of second partial probabilities can be determined, by means of which in turn, the new total correspondence probability for each second representation from the plurality of second representations can be determined.

The plurality of predetermined second representations with respect to the respectively represented can be stored in a database.

Further, a selection frequency for each second representation and/or a number of selection sequences for the second representations stored in the database may be stored in the database.

Also, first representations can be stored in the database, wherein the stored first representations are correlated to selected second representations in the database, wherein the first representations correlated to a second representation are used to determine the similarity of the first representations to a second representation.

The second representation can be replaced by the first representation correlated to the second representation.

The signals may be derived from a neural activity in the brain of a human being.

The signals may be derived from a man-machine-interface arranged outside of the human being.

The first representation of the intended activity is generated from the neural signals.

Further, a database for use in a method according to the invention for the reconstruction of the intended activities is provided, the database being adapted to store second representations that are respectively representative of a predetermined activity, and to select stored second representations according to a predetermined correspondence criterion and compare to first representations, which are generated from a measured neural activity of the brain of a human being.

The database may be further adapted to store the first representations, which have been generated from a measured neural activity of the brain of a human being, and to link the first representations to the second representations stored in the database and/or to replace second representations stored in the database by the first representation.

By means of a selected second representation, a tool, which comprises at least one of a prosthesis, speakers, and display means, may be controlled.

Further, a signal processing means for reconstruction of the intended activity is provided by the invention, which can be coupled to a database, and which comprises an interface, wherein the interface is adapted to receive signals from a man-machine-interface, wherein the signals represent a neural activity of the brain of a human being, and wherein the signal processing means is adapted to generate a first representation wherein the signal processing means is adapted to generate a first representation from neural signals using a predetermined method, determine, for second representations from a plurality of predetermined second representations, which respectively are representative for a predetermined activity, wherein the predetermined second representations are generated from predetermined activities, respectively a degree of correspondence between the respective second representation and the first representation according to a predetermined correspondence criterion, and depending on the degree of correspondence, select a second representation of the neural signals from the plurality of second representations as the second representation representative of the intended activity, and to reconstruct the activity represented by the selected representation as the intended activity.

Advantageous embodiments of the method and the means, respectively, comprise the steps, that prior to a selection of a second representation, it is verified, whether the degree of correspondence satisfies a predetermined criterion, and if the degree of correspondence does not satisfy the predetermined criterion, the intended activity of the first representation is reconstructed. These steps cause only a second representation being selected from the plurality of second representations, if it has at least a minimum correspondence. In contrast, if no correspondence is found amongst the second representations, the intended activity is selected directly from the first representations.

The predetermined method, by means of which the first representation is generated from the neural signals comprises applying a predetermined model, with which a neural brain activity is translated into the intended activity, wherein the entirety of intended activities form a continuous parameter space. This means that the translation is done by means of regressive methods. This translation, therefore, is not a classification in which the indicative brain activity is compared to recorded brain activities which already have been determined by predefined representations.

BRIEF DESCRIPTION OF THE FIGURES

Details and features of the invention as well as concrete embodiments of the invention may be derived from the following description in connection with the drawing which shows.

DETAILED DESCRIPTION OF THE INVENTION

Figure 1:
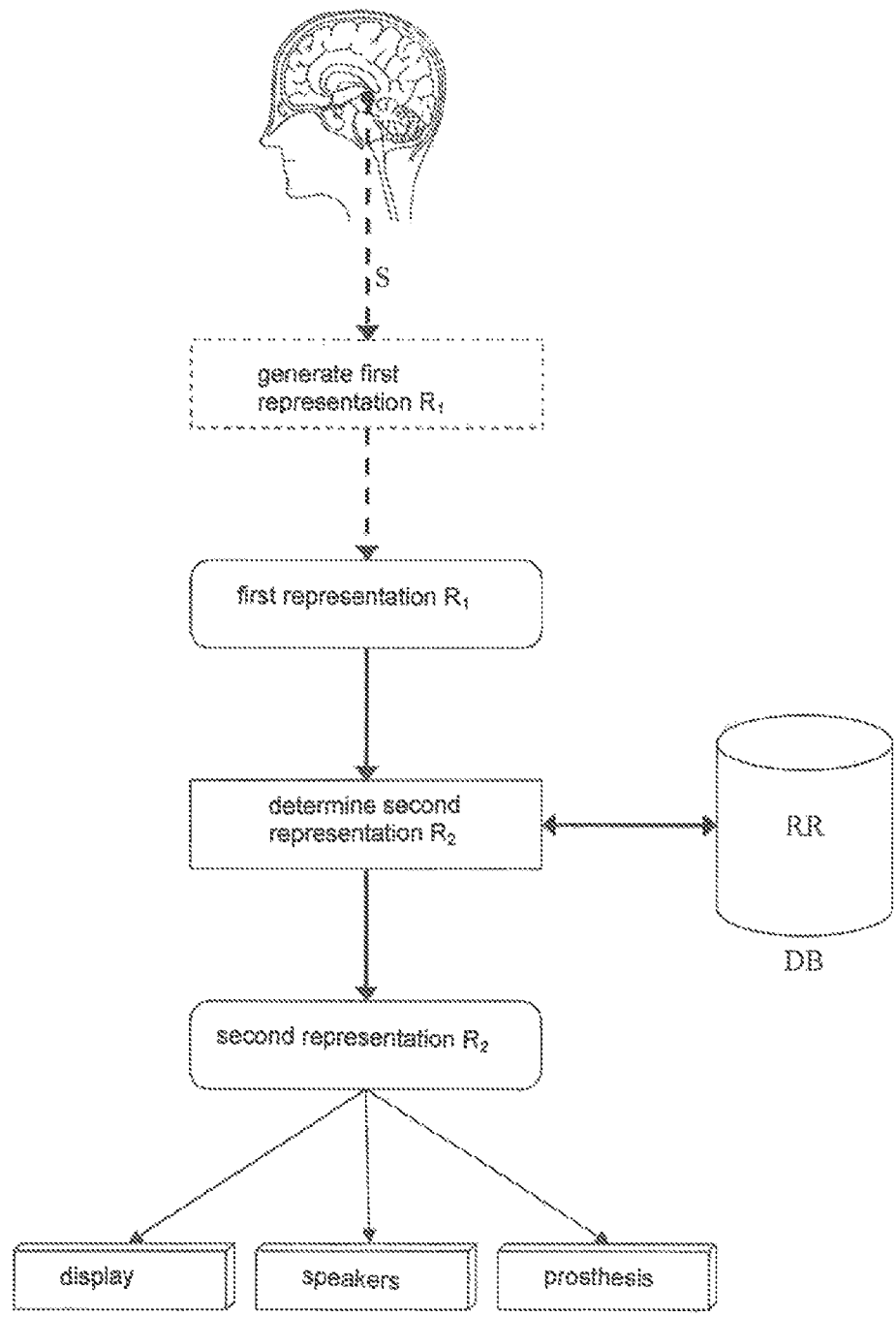
FIG. 1 a block diagram for illustration of the method according to the invention.

The method according to the invention for reconstruction of brain activities of a human being is described below with reference to FIG. 1 in detail.

According to the invention, from a first representation $R_1$ of neural signals S the corresponding intended activity is reconstructed by determining from a number of second representations RR that second representation $R_2$, which corresponds to a certain probability of the first representation $R_1$. The plurality of second representations RR, for example, can be stored in a database DB, and advantageously for each person, a number of individualized second representations RR can be stored.

In a preferred embodiment of the invention, the database always contains a complete set of second representations RR sufficient for the respective application. This means that in the database DB an entirety of second representations RR is stored which is required for the respective application, preferably, individually and situationally appropriate. For example, a database for linguistic communication may contain vowels and consonants occurring in the respective language as well as the words necessary for the application.

Creating the database DB can or should be done with the participation of the respective user. In this case, the user selects from the variety of possible representations the representations which are preferably used by him. A doctor or a technical expert for the respective application or for creating or generating the database specifies the possible representations and verifies the completeness of the user's selection.

While the first representation $R_1$, which has been generated from the neural signals S, has a high fuzziness with respect to the represented activity, the second representations RR stored in the database DB are representations that have no fuzziness. In the following, the first representation $R_1$ will also be referred to as fuzzy representation. In the following, the second representation $R_2$ and all representations stored in the database DB, respectively, will also be referred to as sharp representations.

The first representation $R_1$ is indicative of or describes in a diffuse manner an intended activity of a human being, and has been derived from a neural signal of the brain of the human being concerned. The intended activity may, for example, be an imaginary movement, imaginary language (for example, words or whole sentences), an emotion or a visual impression. The first and diffuse, respectively, reconstruction $R_1$ is generated from the devices known in prior art or by a predetermined method, respectively. This predetermined method, by means of which the first representation is generated from the neural signals comprises applying a predetermined model, by which a neural activity in the brain is translated into the intended activity, wherein the entirety of intended activities form a continuous parameter space. This means that the translation is carried out by means of regressive processes. This translation, therefore, is not a classification in which the indicative brain activity is compared to already determined predefined representations of recorded brain activities.

When determining the second and sharp, respectively, representation $R_2$, a degree of correspondence between the first representation $R_1$ and the second representations RR stored in the database DB is determined according to a predetermined correspondence criterion and then depending on the degree of correspondence, one of the second representations $R_2$ is selected. In a preferred embodiment of the invention that second representation $R_2$ is selected, which can be assigned to the first representation $R_1$ with the highest probability.

The selected second representation $R_2$ can then be transmitted to a means for controlling the tool, wherein the means depending on the type of the second representation of $R_2$ may be, for example, a prosthesis, speakers, or a display device. If the intended activity, for example, is an imaginary movement of the right arm of the person, then the first representation $R_1$ is indicative of the intended movement. The first representation $R_1$, for example, is the trajectory of the right arm. In this case, a second representation $R_2$ is determined from the database DB, which also is indicative of a movement. The second representation $R_2$, also a trajectory of the right arm, is then supplied to the prosthesis, which is to perform the movement of the right arm.

In order to select the one ("best") second representation $R_2$ from the database DB, a degree of correspondence between the respective second and the first representation $R_1$ is respectively determined for the second representations RR stored in the database DB. Then, depending on the degree of correspondence, a second representation $R_2$ is selected from second representations RR stored in the database.

The degree of correspondence can be determined by means of the total correspondence probability $P_i$ for each second representation $R_i$ from the plurality of second representations RR stored in the database DB. The total correspondence probability $P_i$ can be created from a combination of first partial probabilities $TP_i$, wherein for each second representation $R_i$ of the second representations RR stored in the database DB, a number of first partial probabilities $TP_i$ can be generated respectively.

In a preferred embodiment of the method according to the invention, the following first partial probabilities $TP_i$ can be considered for the calculation of the total correspondence probability $P_i$:

first partial probability $TP1_i$ which indicates the frequency of the second representations in the plurality of predetermined second representations RR;

first partial probability $TP2_i$ which is determined on the basis of relationships of the respective second representations with respect to already selected second representations; the relationships can be semantic or historical relationships; and first partial probability $TP3_i$ which indicates the relative similarity of the respective second representation with respect to the first representation.

The first partial probabilities $TP1_i$ to $TP3_i$ can be weighted respectively by a weighting factor $G_i$. The weighting factor $G_i$ can be chosen differently for each partial probability. The total correspondence probability $P_i$ can be calculated, for example, by forming the product over the weighted partial probabilities or by forming the sum over the weighted partial probabilities.

In a subsequent step, that second representation will be selected from the second representations RR stored in the database DB, which has the greatest total correspondence probability P; with respect to the first representation $R_1$.

Because the second representations RR stored in the database are sharp reconstructions or sharp representations, respectively, of intended activities, this method for the first time allows for supplying to a corresponding tool noiseless, i.e. sharp reconstructions of intended movements, speech, emotions, or visual imaginations.

The application of the method according to the invention is explained below with reference to the reconstruction of speech, images and movements of imaginary speech, images or movements, respectively, in more detail.

Reconstruction of Speech:

In the case of reconstruction of speech from neural signals, in the database DB second representations RR in the form of sonograms of the vowels, the consonants, as well as for words or sentences individualized for the respective person are stored. Individualized means in this context:

the sound, in particular, the single consonants and vowels has been recorded by the respective person itself with the own voice. In case the person is not able to speak himself or herself, records or recordings, respectively, may be used also. In case also older records are not available, the sound, in particular, the single consonants and vowels may be derived on the basis of the age, sex, and, if needed, further features may be derived from a standardized database, or alternatively may be generated by the system and may be stored as sonograms in the database DB.

The words to be stored in form of sonograms in the database DB have been selected for or by, respectively, the respective person himself/herself and for his/her needs.

When applying the method according to the invention, the sonograms reconstructed from the brain activity of the person fuzzy and imprecise, respectively, are "translated" into precise and sharp, respectively, sonograms. The sonogram which has been reconstructed imprecisely and fuzzy, respectively, has been generated from the signals S which have been derived from a neural activity of the brain of the person, and form the first representation $R_1$.

A sharp sonogram $R_2$ is selected from the database DB with respect to the imprecise and fuzzy, respectively, reconstructed sonogram $R_1$, wherein at first, probabilities of a sharp sonogram are calculated by means of various first indicators or first partial probabilities, respectively. The first partial probabilities may comprise:

The probabilities of possible vowels, consonants or words, respectively, which have been derived on the basis of the relative frequencies within the database DB (first indicator 1 or first partial probability $TP1_i$, respectively).

The probabilities of possible vowels, consonants, or words, respectively, which are determined on the basis of semantic relationships of the sharp sonograms with respect to other sharp sonograms within the database DB (first indicator 2 or first partial probability $TP2_i$, respectively). For this, the database DB may contain information which indicates for single languages the probabilities of letters, sounds or words on the basis of previous letters, sounds or words, respectively.

The probabilities of possible vowels, consonants, or words, respectively, which have been determined on the basis of a similarity of the sharp sonograms with respect to the fuzzy sonogram $R_1$ (first indicator 3 or first partial probability $TP3_i$, respectively). For this, it may be advantageous, due to the various intonation possibilities, to always determine the similarity of the fuzzy sonogram $R_1$ with respect to the frequency and temporally scaled sharp sonograms wherein the frequency indicates the vocal range and the time, the speaking velocity.

Each of the previously mentioned first indicators or first partial probabilities, respectively, indicates various probabilities for sharp sonograms which may be assigned to the fuzzy sonograms $R_1$.

In the next step, the most probable second representations or sharp sonograms, respectively, are selected from the second representations RR stored in the database by using the above-mentioned first indicators or first partial probabilities, respectively. For this, respectively for vowels, consonants, or words, it is advantageous

- to weigh the first indicators or first partial probabilities $TP_i$, respectively, by a weighting factor $G_i$, wherein the weighting factor for each partial probability may be selected differently, and
- to determine for each second representation or for each sharp sonogram, respectively, in the database DB a relative probability by means of the first indicators or by means of the first partial probabilities, respectively, i.e., a total correspondence probability $P_i$. The total correspondence probability $P_i$ may be formed by combination of the first indicators or the first partial probabilities, respectively. For example, the total correspondence probability $P_i$ may be determined from the sum of the weighed first indicators or the weighed first partial probabilities, respectively, $$P_i = \sum_{i=1}^{n} TP_i \cdot G_i$$

or from the product of the weighed first partial probabilities $$P_i = \prod_{i=1}^{n} TP_i \cdot G_i.$$

In a preferred embodiment of the method according to the invention, after the determination of the relative probabilities or total correspondence probabilities $P_i$, respectively, second indicators or second partial probabilities, respectively, may be calculated using the total correspondence probabilities $P_i$. The second indicators or second partial probabilities, respectively, may comprise:

The probabilities of possible words which are determined on the basis of the previously determined total correspondence probabilities $P_i$ of the vowels and/or consonants (second indicator 4 or second partial probability $TP1_j$, respectively).

The probabilities of possible consonants and/or vowels which are determined on the basis of a previously determined total correspondence probability $P_i$ of the vowels or consonants, respectively (second indicator 5 or second partial probability $TP2_j$).

By using these second indicators or second partial probabilities, respectively, and if needed, by using further indicators or partial probabilities, respectively, the total correspondence probability $P_i$ may be determined again. By means of the newly determined total correspondence probability, that second representation or that sharp sonogram, respectively, may be selected from the database DB which has the greatest total correspondence probability $P_i$. The selected sonogram may be provided for output via a speaker.

In an embodiment of the method according to the invention, it may be advantageous providing a threshold probability. In case the total correspondence probability of the selected sonogram does not exceed the threshold probability, then instead of a sharp sonogram from the database DB, the fuzzy sonogram $R_1$ may be provided for output via a speaker. Usually, however, always at least one sharp consonant, one sharp vowel, or one sharp phoneme should be always available for selection. For this, the threshold probability may preferably be adapted.

Further, the database DB may also comprise breaks or break sounds or emotional sounds, respectively, for example, "Äh" or "Haha". Further, it may be provided for consonants and/or vowels to be replaced or to be augmented by phonemes in the database DB.

Additionally to the partial probabilities and the second partial probabilities mentioned above, further indicators or partial probabilities may be used to determine the respective total correspondence probabilities. For example, a partial probability may be provided which indicates the use frequency of a word depending on a person.

According to a specifically preferred embodiment of the method according to the invention, an optimization or calibration, respectively, method may be provided by means of which the single weighting factors $G_i$ may be adapted or optimized, respectively. The single weighting factors may also be adjusted or adapted, respectively, on the basis of an evaluation through the user.

Reconstruction of Images:

In case of a reconstruction of images (visual image imagination) from neural signals, in the database DB individualized images are stored for the respective person as second representations RR. Preferably, in the database DB such images are stored which are necessary or desired, respectively, for the application intended by the user. For these images, various representations are suitable, also, e.g., illustrations in the spatial frequency domain or in other spectral decompositions.

For example, for a child or a person suffering from autism who uses the images for communication, symbols for a simple communication may be stored in the database DB. In a further example, for a forensic examination, images of persons, actions or locations may be stored in the database DB. According to a further example, for a soldier schematic position illustrations or symbolized coded information may be stored in the database as second representations. For a human being who uses the images for work, for example, technical appliances or figures may be stored as images or second representations, respectively, in the database. In a further example, for a psychological examination, images of emotional expressions, actions or colors may be stored as second representations.

The reconstruction of the imaginary image from the brain activity of a human being, in turn, results from weighed indicators or weighed partial probabilities, respectively, as explained with reference to the reconstruction of speech.

Here, again at first the total correspondence probabilities of the sharp images RR stored in the database DB are calculated on the basis of various first indicators or first partial probabilities, respectively. The first partial probabilities may comprise:

the probabilities of possible images which may be determined on the basis of their frequency in the database DB.

The probabilities of possible images which are determined on the basis of semantic relationships with respect to previous images or already selected images, respectively. For this, corresponding information may be stored in the database DB.

The probabilities of possible images which are determined on the basis of a similarity of the fuzzy image $R_1$ with respect to the sharp images stored in the database DB.

The first indicators or first partial probabilities, respectively, show different probabilities for sharp images from the database DB which may be assigned to the fuzzy image $R_1$.

By using the first indicators or first partial probabilities, respectively, the most probable sharp images are selected from the database DB. For this, in turn a total correspondence probability is determined, wherein the first indicators or first partial probabilities, respectively, are weighed by a weighting factor $G_i$, wherein the weighting factor for each partial probability may be selected differently; and for each second representation RR or for each sharp image, respectively, the relative probability may be determined from the database by means of the weighed first indicators or by means of the first weighed partial probabilities, respectively. For this, in turn, the sum or the product of the weighed partial probabilities may be used, as has been explained previously with reference to the reconstruction of speech.

If needed, further indicators or partial probabilities, respectively, may be used for determining the total correspondence probability. By means of the total correspondence probability, the most probable sharp image $R_2$ is selected from the database DB, and is, for example, provided for output on the display.

Further, also here, a threshold probability may be provided which has to be achieved in order to select the corresponding sharp image from the database DB. In case this threshold probability is not reached, then the fuzzy image $R_1$ may be provided for output to the display.

In a preferred embodiment of the invention, in the database DB, also empty images are stored as second representations RR. Moreover, further indicators or partial probabilities, respectively, may be provided which are used for the calculation of a total correspondence probability. For example, the partial probability may be provided which indicates the use frequency of an image by the user.

Also here, it may be advantageous to adjust a single weighting factor by means of an optimization or calibration, respectively, method. This can also be effected on the basis of an evaluation through the user.

Reconstruction of Movements:

When reconstructing movements from neural signals, in the database, individualized movements are stored for the respective person as second representations RR. Preferably, such movements are stored which are necessary or desired, respectively, for the application intended by the user.

For example, for a strongly paralyzed person who would like to control an internet browser by means of a computer mouse, movement trajectories to the respectively currently possible hyperlinks, right, left or double-click as well as scrolling of the screen downwards or upwards may be stored. For the human being who wants to control an artificial arm, the database may store movement trajectories with respect to objects which are within one's reach as well as grips, for example, precision grip, power grip, etc. currently detected by a camera may be stored. For example, in case an object has been grasped, it may be advantageous to alter the database or to only provide such second representations for selection which represent movement trajectories at possible target points for placing the grasped object within a space. In a further example, for a human being who would like to control a vehicle with an integrated camera possible driving directions, turns, a stop or acceleration may be stored in the database as second representations.

For the reconstruction of imaged movements from the brain activity of a human being, a total correspondence probability is determined, as explained with reference to the reconstruction of speech and images.

Hereby, at first indicators or first partial probabilities, respectively, are determined from which in turn a total correspondence probability is determined. The first indicators or first partial probabilities, respectively, may comprise:

The probabilities of possible movements which are determined on the basis of frequency of the movements in the database DB.

The probabilities of possible movements which are determined on the basis of semantic relationships of the respective second representation in the database with respect to previous movements or already selected movements, respectively. For this, in the database, possible or at least typical movement sequences may be stored. This information and further information on the surroundings may be used in order to delimit the currently possible movements. This indicator or this partial probability, respectively, provides particular dynamics to the database DB, because depending on the current situation or depending on the previous movements, certain movements may be excluded in the database DB.

The probabilities of possible movements which are determined on the basis of the similarity of a respective sharp movement in the database DB with respect to the fuzzy movement $R_1$.

Each of these first indicators or each of these first partial probabilities, respectively, indicate various probabilities for the assignment of the sharp movement to the fuzzy movement $R_1$.

In a subsequent step, from the first partial probabilities or first indicators, respectively, total correspondence probabilities for the respective sharp movements are determined in the database DB. For determining the total correspondence probabilities the indicators or the partial probabilities, respectively, are weighed by a weighting factor $G_i$, wherein the weighting factor for each partial probability may be selected differently, and for each sharp movement in the database DB, the total correspondence probability or relative probability, respectively, is determined by means of the indicators. For this, in turn, the sum of the weighed indicators or weighed partial probabilities, respectively, or the product of the weighed indicators or weighed partial probabilities, respectively, may be formed.

In a preferred embodiment of the invention, in the database, additionally to single movements or partial movements, respectively, also complete movements, for example, in the form for trajectories with target and endpoints as well as partial movements may be stored. In this case, analogously to the reconstruction of speech, the indicators or partial probabilities for the complete movements and for the partial movements may be used for the determination of the total correspondence probability.

On the basis of the determined total correspondence probabilities, then, the second indicators or the second partial probabilities, respectively, may be calculated. The second partial probabilities may comprise:

the probabilities of possible movements which are determined on the basis of the previously determined total correspondence probability of the complete movement; and the probabilities of possible movements which are determined on the basis of the previously determined total correspondence probabilities of the partial movements.

By using the second indicators or second partial probabilities, respectively, the total correspondence probability may be determined again. If needed, also further second indicators or partial probabilities, respectively, may be considered.

In a next step, the sharp movement having the greatest total correspondence probability is selected from the database DB.

Also, when reconstructing movements, it may be advantageous to provide a threshold probability. As far as the total correspondence probability of the sharp movement to be selected from the database DB does not exceed this threshold probability, the fuzzy movement $R_1$ may be provided for control, for example, of a prosthesis. It may be advantageous, if the threshold probability may be adapted according to a concrete situation. This is also advantageous for the reconstruction of speech or images, respectively.

In the database DB, also second representations of movement breaks may be stored. Moreover, further first or second partial probabilities, respectively, may be provided for a calculation of the respective total correspondence probability. For example, a partial probability may be provided which indicates the probability of a movement according to the use frequency of the movement by the user. Also, it may be advantageous, if the weighting factors are adjusted according to an optimization or calibration procedure. The adjustment of the weighting factors may also be performed by the user.

In a preferred embodiment of the invention, it is also possible to store in the database second representations of speech as well as also second representations of images and movements. Thereby, it is possible to reconstruct according to each situation speech, images and/or movements from neural signals, and to provide them for a corresponding tool, for example, a display device, speakers or prostheses.

The database DB may also be adapted to update frequencies and/or sequences of the used second representations (vowels, consonants, words, images and/or movements). Thereby, an adaptive, i.e., self-teaching database can be realized for storing second representations.

In a further embodiment of the database DB, also the first representations $R_1$ can be stored in the latter, and/or the stored fuzzy representations $R_1$ of one or more sharp representations $R_2$ from RR may be assigned in the database DB. This has the advantage that for example, the similarity between a first generated representation $R_1$ and a second representation $R_2$ can be determined in the database DB, wherein at first, a similarity between the generated first representation $R_1$ and a first representation stored in the database may be determined. The most similar first representation stored in the database may then be used in order to select the second representation in the database which is linked thereto as second representation which is similar to the generated first representation $R_1$.

Further, it may also be advantageous to replace second representations stored in the database by generated first representations $R_1$ such that from a generated fuzzy first representation $R_1$ a sharp representation $R_2$ is created in the database DB. The updating or adjustment, respectively, of the database may optionally be effected automatically or only after a positive evaluation by the user. In this way, the database DB may be updated, e.g., with respect to neural signals which change over time.

Figure 2:
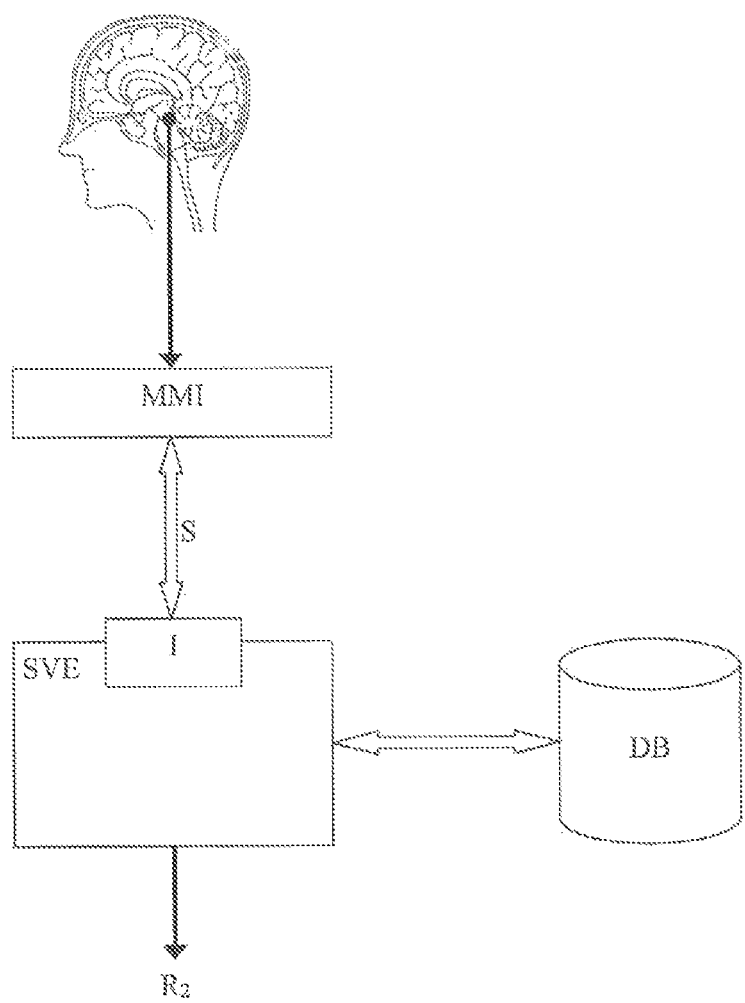
FIG. 2 a schematic arrangement of a signal processing unit according to the invention as well as the coupling of the signal processing means to a database according to the invention and a man-machine-interface.

FIG. 2 shows a schematic block diagram of a signal processing means SVE for reconstruction of intended activities according to the invention.

The signal processing means SVE comprises an interface I which is adapted to receive signals from a man-machine-interface MMI. The man-machine-interface MMI preferably is adapted to derive from neural activities of the human being neural signals S, and to transfer these to the interface of the signal processing means SVE.

The signal processing means SVE, in particular, is adapted to carry out the method for reconstruction of intended activities according to the invention. For this, the signal processing means SVE is coupled to a database DB. In a particular embodiment of the signal processing means SVE, the latter may also comprise the database DB, for example, as an embedded database. Further, the signal processing means SVE comprises an interface for output of the reconstructed intended activities or the determined second representation, respectively.

The described embodiments of the method or the means, respectively, comprise the steps that prior to a selection of the second representation, it is verified, whether the degree of correspondence of a predetermined criterion is complied with, and, as far as the degree of correspondence does not comply with the predetermined criterion, the intended activity is reconstructed from the first representation. These steps cause a second representation being only selected from the plurality of second representations, if the latter has at least a minimum correspondence. If, however, no matching one is found amongst the second representations, the intended activity is directly selected from the first representation.

The invention claimed is:

1. A method for reconstruction of intended activities from a first representation of neural signals which is indicative of an intended activity, wherein the first representation is generated using a predetermined method from the neural signals, for each second representation from a plurality of predetermined second representations, each of which being representative of a predetermined activity, wherein the plurality of predetermined second representation are generated from predetermined activities, a degree of correspondence is determined respectively between each of the respective second representations and the first representation according to a predetermined correspondence criterion, and depending on the degree of correspondence, a single second representation of the neural signals from the plurality of second representations is selected as the second representation representative of the intended activity, and the activity represented by the selected representation is reconstructed as the intended activity, wherein the determination of the degree of correspondence in accordance with the correspondence criterion comprises a determination of a total correspondence probability for each second representation from the plurality of second representations, wherein the total correspondence probability from a combination of first partial probabilities, which are created for each second representation from the plurality of second representations and wherein the total correspondence probability for each second representation indicates the probability with which the respective second representation of the first representation is assignable, and wherein forming the first partial probabilities comprises at least one of determining a partial probability based on the frequency of the second representation within the plurality of predetermined second representations, determining a partial probability based on semantic relationships of the second representation to already selected second representations, and determining a partial probability based on a similarity of the second representation to the first representation.

2. The method of claim 1, wherein the second representation with the greatest total correspondence probability selected.

3. The method of claim 1, wherein each of the first partial probabilities is weighted by a weighting factor, wherein the weighting factor can be selected differently for each partial probability.

4. The method of claim 1, wherein prior to the selection of the second representation from the plurality of second representations, it is verified whether the total correspondence probability of the second representation to be selected exceeds a predetermined threshold, and wherein when the predetermined threshold is not exceeded, the first representation the reconstructed intended activity.

5. The method of claim 1, wherein on the basis of the respectively determined total correspondence probability, a number of second partial probabilities is determined, with which in turn a new total correspondence probability for each second representation from the plurality of second representations is determined.

6. The method of claim 1, wherein the plurality of predetermined second representations is stored in a database.

7. A method of for reconstruction of intended activities from a first representation of neural signals which is indicative of an intended activity, wherein the first representation is generated using a predetermined method from the neural signals, for each second representation from a plurality of predetermined second representations, each of which being representative of a predetermined activity, wherein the plurality of predetermined second representation are generated from predetermined activities, a degree of correspondence is determined respectively between each of the respective second representations and the first representation according to a predetermined correspondence criterion, and depending on the degree of correspondence, a single second representation of the neural signals from the plurality of second representations is selected as the second representation representative of the intended activity, and the activity represented by the selected representation is reconstructed as the intended activity, wherein plurality of predetermined second representations is stored in a database, and wherein for each second representation, a selection frequency, and/or for the second representations stored in the database, a number of selection sequences is stored in the database.

8. The method of claim 7, wherein first representations are stored in the database, and wherein the stored first representations are correlated in the database to selected second representations, wherein first representations correlated to a second representation are used to determine the similarity of the first representations a second representation.

9. The method of claim 8, wherein the second representation is replaced by the first representation which has been correlated to the second representation.

10. The method of claim 1, wherein the first representations and the second representations comprise at least one out of movements, speech, emotions, pictures, smells, and tactile sense.

11. The method of claim 1, wherein the signals are derived from a neural activity of the brain of a human being.

12. The method of claim 11, wherein the signals are derived from a man-machine-interface arranged outside the human being.

13. The method of claim 1, wherein prior to selecting a second representation, it is verified whether the degree of correspondence satisfies a predetermined criterion, and if the degree of correspondence does not satisfy the predetermined criterion, the intended activity is reconstructed from the first representation.

14. The method of claim 1, wherein the predetermined method comprises applying a predetermined model, with which a neural brain activity is translated into the intended activity, wherein the total of intended activities forms a continuous parameter space.

15. A database for use in a method for reconstructing intended activities according to claim 1, wherein the database is adapted to store second representations, which respectively are representative of a predetermined activity, and to select stored second representations according to a predetermined correspondence criterion and compare them to first representations, which are generated from a measured neural activity of the brain of a human being.

16. The database of claim 15, wherein the database is further adapted to store first representations, which have been generated from a measured neural activity of the brain of a human being, and to link the first representations to the second representations stored in the database and/or replace second representations stored in the database by the first representation.

17. The method of claim 1, wherein a tool comprising at least one out of a prosthesis, speakers and display means is controlled by a selected second representation.

18. The method of claim 1, wherein each one of the representations respectively represents a sonogram.

19. The method of claim 1, wherein each one of the representations respectively represents a trajectory of motions.

20. The method of claim 1, wherein each one of the representations respectively is an image representation.

21. The method of claim 7, wherein the first representations and the second representations comprise at least one out of movements, speech, emotions, pictures, smells, and tactile sense.

22. The method of claim 7, wherein the signals are derived from a neural activity of the brain of a human being.

23. The method of claim 7, wherein a tool comprising at least one out of a prosthesis, speakers and display means is controlled by a selected second representation.

24. The method of claim 7, wherein each one of the representations respectively represents a trajectory of motions.

25. The method of claim 7, wherein each one of the representations respectively is an image representation.

* * * * *